(12) United States Patent
Morini et al.

(10) Patent No.: US 6,605,562 B1
(45) Date of Patent: Aug. 12, 2003

(54) COMPONENTS AND CATALYSTS FOR THE POLYMERIZATION OF OLEFINS

(75) Inventors: Giampiero Morini, Padova (IT); Giulio Balbontin, Ferrara (IT); Yuri V. Gulevich, Elkton, MD (US)

(73) Assignee: Basell Poliolefine Italia S.p.A., Milan (IT)

(*) Notice: Subject to any disclaimer, the term of this patent is extended or adjusted under 35 U.S.C. 154(b) by 0 days.

(21) Appl. No.: 09/582,600

(22) PCT Filed: Oct. 22, 1999

(86) PCT No.: PCT/EP99/08018

§ 371 (c)(1),
(2), (4) Date: Jun. 28, 2000

(87) PCT Pub. No.: WO00/26259

PCT Pub. Date: May 11, 2000

(30) Foreign Application Priority Data

Nov. 4, 1998 (EP) .............................. 98203733

(51) Int. Cl.$^7$ .......................... C08F 10/06; C08F 4/649
(52) U.S. Cl. ....................... 502/127; 502/118; 502/128; 526/124.2; 526/124.9; 526/125.3
(58) Field of Search ................. 502/118, 127, 502/128

(56) References Cited

U.S. PATENT DOCUMENTS

| | | | |
|---|---|---|---|
| 4,220,554 A | 9/1980 | Scata et al. | 252/429 B |
| 4,298,718 A | 11/1981 | Mayr et al. | 526/125 |
| 4,399,054 A | 8/1983 | Ferraris et al. | 252/429 B |
| 4,469,648 A | 9/1984 | Ferraris et al. | 264/9 |
| 4,495,338 A | 1/1985 | Mayr et al. | 526/125 |
| 5,459,116 A | 10/1995 | Ro et al. | 502/115 |
| 5,463,111 A | 10/1995 | Steffen | 560/192 |
| 5,569,780 A | 10/1996 | Steffen | 560/192 |

FOREIGN PATENT DOCUMENTS

| | | |
|---|---|---|
| DE | 2822472 | 12/1978 |
| DE | 4326918 | 1/1995 |
| EP | 0045977 | 2/1982 |
| EP | 0086473 | 8/1983 |
| EP | 0086644 | 8/1983 |
| EP | 0372836 | 6/1990 |
| EP | 0382206 | 8/1990 |
| EP | 0395083 | 10/1990 |
| EP | 0553805 | 8/1993 |
| EP | 0553806 | 8/1993 |
| EP | 0601525 | 6/1994 |
| EP | 0641807 | 3/1995 |
| EP | 0749984 | 12/1996 |
| GB | 1322640 | 7/1973 |
| GB | 1572669 | 7/1980 |
| JP | 8157521 | 6/1996 |
| WO | 9616092 | 5/1996 |
| WO | 9844001 | 10/1998 |

OTHER PUBLICATIONS

J. March, *Advanced Organic Chemistry*, pp. 771–781 (1992).
W. Lehnert, "Knoevenagel–Kondensationen Mit $TiCl_4$/Base–III," *Tetrahedron*, vol. 29, 635–638 (1973).
J. Lehmann et al., "Regiocontrol and Stereoselectivity in Tungsten–Bipyridine Catalysed Allylic Alkylation," *Tetrahedron*, vol. 51, No. 32, 8863–8874 (1995).
Shima, Takeo et al., "Malonic Ester Catalysts for the Preparation of Polyesters," Chemical Abstract No. 25763, vol. 76, No. 6 (Feb. 7, 1972).
JP Abstract No. 46 027180(B) (Aug. 5, 1971); Authors: Takeo Shima & Isao Oka; Title: Malonic Ester Catalysts for the Preparation of Polyesters.

Primary Examiner—David W. Wu
Assistant Examiner—Caixia Lu

(57) ABSTRACT

The present invention relates to catalyst components for the polymerization of olefins, and to the catalyst obtained therefrom, particularly suitable for the stereospecific polymerization of olefins, comprising Ti, Mg, halogen and an electron donor compound selected from heteroatom containing esters of malonic acids (heteroatom containing malonates). Said catalyst components when used in the polymerization of olefins, and in particular of propylene, are capable to give polymers in high yields and with high isotactic index expressed in terms of high xylene insolubility.

14 Claims, No Drawings

COMPONENTS AND CATALYSTS FOR THE POLYMERIZATION OF OLEFINS

The present invention relates to catalyst components for the polymerization of olefins, to the catalysts obtained therefrom and to the use of said catalysts in the polymerization of olefins $CH_2=CHR$ in which R is hydrogen or a hydrocarbyl radical with 1–12 carbon atoms. In particular the present invention relates to catalyst components, suitable for the stereospecific polymerization of olefins, comprising Ti, Mg, halogen and an electron donor compound selected from heteroatom containing esters of malonic acids (heteroatom containing malonates). Said catalyst components when used in the polymerization of olefins, and in particular of propylene, are capable to give polymers in high yields and with high isotactic index expressed in terms of high xylene insolubility.

The use of some esters of malonic acid as internal electron donors in catalysts for the polymerization of propylene is already known in the art.

In EP-A-45977 is disclosed the use of an ester of malonic acid (diethyl 2,2-diisobutylmalonate) as internal donor of a catalyst for the polymerization of olefins. EP-A-86473 discloses a catalyst for the polymerization of olefins comprising (a) an Al-alkyl compound, (b) an electron donor compound having certain reactivity features towards $MgCl_2$ and (c) a solid catalyst component comprising, supported on $MgCl_2$, a Ti halide and an electron donor selected from many classes of ester compounds including malonates. None of the above-cited applications discloses malonates containing heteroatoms. The same applies to EP-A-86644 that discloses the use of diethyl 2-n-butyl malonate and diethyl 2-isopropylmalonate as internal donors in Mg-supported catalysts for the polymerization of propylene.

It is apparent from the analysis of the polymerization results reported in the above-mentioned applications that a common drawback experienced in the use of the mentioned malonates was represented by a still unsatisfactory polymerization yield and/or a not suitable isotactic index of the final polymer. This is confirmed also by the disclosure of JP-08157521. This application relates to a process for preparing a solid catalyst component for polymerization of olefins which is characterized by contacting a solid catalyst component produced by the reaction among a magnesium compound, a titanium compound and an halogen compound, with one or more electron donating compounds represented by the general formula:

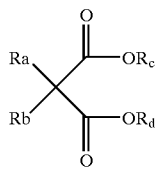

wherein $R_c$ and $R_d$ are, the same or different, a straight-chain or branched-chain hydrocarbon group having 1–10 carbon atoms, and $R_a$ and $R_b$ are the same or different, a saturated or cyclic saturated hydrocarbon group containing one or more secondary or tertiary carbons and having 3–20 carbon atoms. Although an improvement in terms of yields and isotactic index over the previously cited documents is obtained, the results are still not satisfactory for an economical use of the catalyst components disclosed therein.

It has now surprisingly been found that the polymerization yields and the isotactic index of the polymer can be improved by using catalyst components comprising heteroatom containing malonates as internal donors.

It is therefore an object of the present invention to provide a solid catalyst component for the polymerization of olefins $CH_2=CHR$ in which R is hydrogen or a hydrocarbon radical with 1–12 carbon atoms, comprising Mg, Ti, halogen and an heteroatom containing malonate.

The term heteroatom means any atom, different from C and H, in addition to the oxygen atoms deriving from the malonic acid.

In particular, the electron donor compounds can be selected from esters of malonic acids of formula (I):

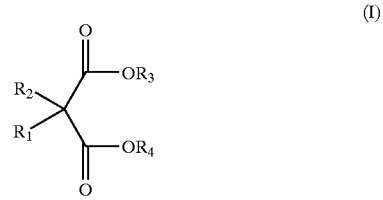

wherein $R_1$ and $R_2$ equal to or different from each other, are H or a $C_1$–$C_{20}$ linear or branched alkyl, alkenyl, cycloalkyl, aryl, arylalkyl or alkylaryl group and said $R_1$ and $R_2$ can also be joined to form a cyclic group; $R_3$ and $R_4$ are independently selected from $C_1$–$C_{20}$ linear or branched alkyl, alkenyl, cycloalkyl, aryl, arylalkyl or alkylaryl group and $R_3$ and $R_4$ can also be joined to form a cyclic group; with the proviso that at least one of the $R_1$ to $R_4$ groups contains at least one heteroatom selected from the group consisting of halogens, N, O, Si, Ge, P, and S.

The heteroatoms, are preferably selected from the group consisting of F, Cl, Br, and Si, and, in a preferred embodiment, they are contained in the $R_1$ or $R_2$ groups.

Preferably, $R_3$ and $R_4$ are primary alkyl, arylalkyl or alkylaryl groups having from 2 to 8 carbon atoms which may contain heteroatoms. More preferably, they are primary branched alkyl groups optionally containing heteroatoms. Examples of suitable $R_3$ and $R_4$ groups not containing heteroatoms are methyl, ethyl, n-propyl, n-butyl, isobutyl, neopentyl, 2-ethylhexyl. Examples of suitable $R_3$ and $R_4$ groups containing heteroatoms are 2-chloroethyl, 1-trifluoromethylethyl, 2-trifluoromethylpropyl 2-trimethylsilylethyl, 2-bromoethyl, 2-trifluoromethylpropyl, 4-chlorobenzyl, 2-fluoroethyl, 3-trimethylsilylallyl.

$R_2$ is preferably, and particularly when $R_1$ is H, a linear or branched $C_3$–$C_{20}$ alkyl, cycloalkyl, arylalkyl group; more preferably $R_2$ is a $C_3$–$C_{20}$ secondary alkyl, cycloalkyl, or arylalkyl. Particularly preferred are also compounds of formula (I) in which $R_1$ is H and $R_2$ is a $C_5$–$C_{20}$ primary linear or branched alkyl, a $C_5$–$C_{20}$ cycloalkyl, a $C_7$–$C_{20}$ arylalkyl or alkylaryl group.

Preferably $R_2$ contains at least one heteroatom. Specific examples of suitable monosubstituted malonate compounds are diethyl 2-(1-trifluoromethylethyl)malonate, diethyl 2-(1-trifluoromethylethylidene)malonate, bis(2-chloroethyl) 2-isopropylmalonate, diethyl 2-(trimethylsilylmethyl) malonate, diethyl 2-p-chlorobenzylmalonate, diethyl 2-piperidylmalonate, diethyl 2-(2-ethylpiperidyl)malonate, diethyl 2-(1-trifluoromethyl-1-methylethyl)malonate, diethyl 2-α-phenyl-p-(trifluoromethyl)benzyl malonate, bis (2-fluoroethyl) 2-isopropylmalonate, bis(2-fluoroethyl) 2-ethylmalonate.

Among disubstituted malonates preferred compounds are those in which at least one of $R_1$ and $R_2$ is a primary $C_3$–$C_2$, alkyl, cycloalkyl, arylalkyl group.

Specific examples of suitable disubstituted malonate compounds are: diethyl-2(1-trifluoromethylethyl)-2- benzylmalonate, diethyl 2-(1-trifluoromethylethyl)-2-methylmalonate, diethyl 2-methyltrimethylsilyl-2-methylmalonate, diethyl 2-p-chlorobenzyl-2-isopropylmalonate, diethyl 2-piperidyl-2-methylmalonate, diethyl 2-(1-trifluoromethyl-1-methylethyl)-2-methylmalonate, bis(2-trimethylsilylethyl) 2-isopropyl-2-isobutylmalonate bis(p-chlorobenzyl) 2-cyclohexyl-2-methylmalonate.

It has been surprisingly found that catalyst components in which the internal donor is a heteroatom containing malonate perform better, in term of yields and isotactic index, than catalyst components comprising analogous malonates not containing heteroatoms.

As explained above, catalyst components according to the invention comprise, in addition to the above electron donor, Ti, Mg and halogen. In particular, the catalyst component comprises a titanium compound, having at least a Ti-halogen bond and the above mentioned electron donor compound supported on a Mg halide. The magnesium halide is preferably $MgCl_2$ in active form which is widely known from the patent literature as a support for Ziegler-Natta catalysts. Patents U.S. Pat. No. 4,298,718 and U.S. Pat. No. 4,495,338 were the first to describe the use of these compounds in Ziegler-Natta catalysis. It is known from these patents that the magnesium dihalides in active form used as support or co-support in components of catalysts for the polymerization of olefins are characterized by X-ray spectra in which the most intense diffraction line that appears in the spectrum of the non-active halide is diminished in intensity and is replaced by a halo whose maximum intensity is displaced towards lower angles relative to that of the more intense line.

The preferred titanium compounds used in the catalyst component of the present invention are $TiCl_4$ and $TiCl_3$; furthermore, also Ti-haloalcoholates of formula $Ti(OR)_{n-y}X_y$, SEQ. ID. NO:5 where n is the valence of titanium and y is a number between 1 and n, can be used.

The preparation of the solid catalyst component can be carried out according to several methods.

According to one of these methods, the magnesium dichloride in an anhydrous state and the heteroatom containing malonate are milled together under conditions in which activation of the magnesium dichloride occurs. The so obtained product can be treated one or more times with an excess of $TiCl_4$ at a temperature between 80 and 135° C. This treatment is followed by washings with hydrocarbon solvents until chloride ions disappear. According to a further method, the product obtained by co-milling the magnesium chloride in an anhydrous state, the titanium compound and the heteroatom containing malonate is treated with halogenated hydrocarbons such as 1,2-dichloroethane, chlorobenzene, dichloromethane etc. The treatment is carried out for a time between 1 and 4 hours and at temperature of from 40° C. to the boiling point of the halogenated hydrocarbon. The product obtained is then generally washed with inert hydrocarbon solvents such as hexane.

According to another method, magnesium dichloride is preactivated according to well known methods and then treated with an excess of $TiCl_4$ at a temperature of about 80 to 135° C. which contains, in solution, a heteroatom containing malonate. The treatment with $TiCl_4$ is repeated and the solid is washed with hexane in order to eliminate any non-reacted $TiCl_4$.

A further method comprises the reaction between magnesium alcoholates or chloroalcoholates (in particular chloroalcoholates prepared according to U.S. Pat. No. 4,220,554) and an excess of $TiCl_4$ comprising the heteroatom containing malonate in solution at a temperature of about 80 to 120° C.

According to a preferred method, the solid catalyst component can be prepared by reacting a titanium compound of formula $Ti(OR)_{n-y}X_y$, where n is the valence of titanium and y is a number between 1 and n, preferably $TiCl_4$, with a magnesium chloride deriving from an adduct of formula $MgCl_2 \cdot pROH$, where p is a number between 0.1 and 6 and R is a hydrocarbon radical having 1–18 carbon atoms. The adduct can be suitably prepared in spherical form by mixing alcohol and magnesium chloride in the presence of an inert hydrocarbon immiscible with the adduct, operating under stirring conditions at the melting temperature of the adduct (100–130° C.). Then, the emulsion is quickly quenched, thereby causing the solidification of the adduct in form of spherical particles. Examples of spherical adducts prepared according to this procedure are described in U.S. Pat. No. 4,399,054 and U.S. Pat. No. 4,469,648. The so obtained adduct can be directly reacted with the Ti compound or it can be previously subjected to thermal controlled dealcoholation (80–130° C.) so as to obtain an adduct in which the number of moles of alcohol is generally lower than 3 preferably between 0.1 and 2.5. The reaction with the Ti compound can be carried out by suspending the adduct (dealcoholated or as such) in cold $TiCl_4$ (generally 0° C.); the mixture is heated up to 80–130° C. and kept at this temperature for 0.5–2 hours. The treatment with $TiCl_4$ can be carried out one or more times. The heteroatom containing malonate can be added during the treatment with $TiCl_4$. The treatment with the electron donor compound can be repeated one or more times.

The preparation of catalyst components in spherical form is described for example in European Patent Applications EP-A-395083, EP-A-553805, EP-A-553806, EP-A-601525 and WO98/44001.

The solid catalyst components obtained according to the above method show a surface area (by B.E.T. method) generally between 20 and 500 $m^2/g$, and preferably between 50 and 400 $m^2/g$, and a total porosity (by B.E.T. method) higher than 0.2 $cm^3/g$, preferably between 0.2 and 0.6 $cm^3/g$. The porosity (Hg method) due to pores with radius up to 10.000 Å generally ranges from 0.3 to 1.5 $cm^3/g$, preferably from 0.45 to 1 $cm^3/g$.

A further method to prepare the solid catalyst component of the invention comprises halogenating magnesium dihydrocarbyloxide compounds, such as magnesium dialkoxide or diaryloxide, with solution of $TiCl_4$ in aromatic hydrocarbon (such as toluene, xylene etc.) at temperatures between 80 and 130° C. The treatment with $TiCl_4$ in aromatic hydrocarbon solution can be repeated one or more times, and the heteroatom containing malonate is added during one or more of these treatments.

In any of these preparation methods the desired heteroatom containing malonate can be added as such or, in an alternative way, it can be obtained in situ by using an appropriate precursor capable to be transformed in the desired electron donor compound by means, for example, of known chemical reactions such as esterification, transesterification etc. Generally, the heteroatom containing malonate is used in molar ratio with respect to the $MgCl_2$ of from 0.01 to 1 preferably from 0.05 to 0.5.

The solid catalyst component according to the present invention are converted into catalysts for the polymerization of olefins by reacting them with organoaluminum compounds according to known methods.

In particular, it is an object of the present invention a catalyst for the polymerization of olefins $CH_2$=CHR, in which R is hydrogen or a hydrocarbyl radical with 1–12 carbon atoms, comprising the product of the reaction between:

(a) a solid catalyst component comprising a Mg, Ti and halogen as essential elements and an heteroatom containing ester of malonic acids;
(b) an alkylaluminum compound and, optionally,
(c) one or more electron-donor compounds (external donor).

The alkyl-Al compound (b) is preferably selected from the trialkyl aluminum compounds such as for example triethylaluminum, triisobutylaluminum, tri-n-butylaluminum, tri-n-hexylaluminum, tri-n-octylaluminum. It is also possible to use mixtures of trialkylaluminum's with alkylaluminum halides, alkylaluminum hydrides or alkylalurninum sesquichlorides such as AlEt$_2$Cl and Al$_2$Et$_3$Cl$_3$.

The external donor (c) can be of the same type or it can be different from the heteroatom containing malonate. Suitable external electron-donor compounds include silicon compounds, ethers, esters such as ethyl 4-ethoxybenzoate, amines, heterocyclic compounds and particularly 2,2,6,6-tetramethyl piperidine, ketones and the 1,3-diethers of the general formula (II):

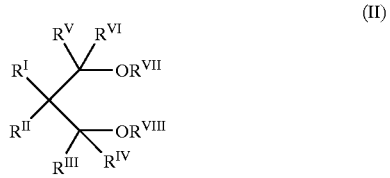

(II)

wherein $R^I$, $R^{II}$, $R^{III}$, $R^{IV}$, $R^V$ and $R^{VI}$ equal or different to each other, are hydrogen or hydrocarbon radicals having from 1 to 18 carbon atoms, and $R^{VII}$ and $R^{VIII}$, equal or different from each other, have the same meaning of $R^{I-RVI}$ except that they cannot be hydrogen; one or more of the $R^{I-RVIII}$ groups can be linked to form a cyclic group. Particularly preferred are the 1,3-diethers in which $R^{VII}$ and $R^{VIII}$ are selected from $C_1$–$C_4$ alkyl radicals.

Another class of preferred external donor compounds is that of silicon compounds of formula $R_a^5R_b^6Si(OR^7)_c$, where a and b are integer from 0 to 2, c is an integer from 1 to 3 and the sum (a+b+c) is 4; $R^5$, $R^6$, and $R^7$, are alkyl, cycloalkyl or aryl radicals with 1–18 carbon atoms optionally containing heteroatoms. Particularly preferred are the silicon compounds in which a is 1, b is 1, c is 2, at least one of $R^5$ and $R^6$ is selected from branched alkyl, cycloalkyl or aryl groups with 3–10 carbon atoms optionally containing heteroatoms and $R^7$ is a $C_1$–$C_{10}$ alkyl group, in particular methyl. Examples of such preferred silicon compounds are methylcyclohexyldimethoxysilane, diphenyldimethoxysilane, methyl-t-butyldimethoxysilane, dicyclopentyldimethoxysilane, 2-ethylpiperidinyl-2-t-butyldimethoxysilane and 1,1,1,trifluoropropyl-2-ethylpiperidinyl-dimethoxysilane. Moreover, are also preferred the silicon compounds in which a is 0, c is 3, $R^6$ is a branched alkyl or cycloalkyl group, optionally containing heteroatoms, and $R^7$ is methyl. Examples of such preferred silicon compounds are cyclohexyltrimethoxysilane, t-butyltrimethoxysilane and thexyltrimethoxysilane.

The electron donor compound (c) is used in such an amount to give a molar ratio between the organoaluminum compound and said electron donor compound (c) of from 0.1 to 500, preferably from 1 to 300 and more preferably from 3 to 100. As previously indicated, when used in the (co) polymerization of olefins, and in particular of propylene, the catalysts of the invention allow to obtain, with high yields, polymers having a high isotactic index (expressed by high xylene insolubility X.I.), thus showing an excellent balance of properties. This is particularly surprising in view of the fact that, as it can be seen from the comparative examples here below reported, the use as internal electron donors of malonate compounds not containing heteroatoms gives worse results in term of yields and/or xylene insolubility.

Therefore, it constitutes a further object of the present invention a process for the (co)polymerization of olefins CH$_2$=CHR, in which R is hydrogen or a hydrocarbyl radical with 1–12 carbon atoms, carried out in the presence of a catalyst comprising the product of the reaction between:
(a) a solid catalyst component comprising a Mg, Ti, halogen and a heteroatom containing malonate;
(b) an alkylatuminum compound and, optionally,
(c) one or more electron-donor compounds (external donor).

Said polymerization process can be carried out according to known techniques for example slurry polymerization using as diluent an inert hydrocarbon solvent, or bulk polymerization using the liquid monomer (for example propylene) as a reaction medium. Moreover, it is possible to carry out the polymerization process in the gas-phase operating in one or more fluidized or mechanically agitated bed reactors.

The polymerization is generally carried out at temperature of from 20 to 120° C., preferably of from 40 to 80° C. When the polymerization is carried out in the gas-phase the operating pressure is generally between 0.5 and 10 MPa, preferably between 1 and 5 MPa. In the bulk polymerization the operating pressure is generally between 1 and 6 MPa preferably between 1.5 and 4 MPa. Hydrogen or other compounds capable to act as chain transfer agents can be used to control the molecular weight of polymer.

The following examples are given in order to better illustrate the invention without limiting it.

CHARACTERIZATIONS

The malonates used in the present invention were prepared by Knoevenagel condensation of halogenated ketones with diethyl malonate, see Tetrahedron, 29, 635, (1973), followed by selective reduction of the double bond, (J. March in "Advanced Organic Chemistry" IV Ed. (1992) pp. 771–781). The malonates having the alcoholic moiety different from ethyl were prepared by transesterification of the corresponding diethyl malonate as described in Example 1 of DE 2822472.

Propylene General Polymerization Procedure

In a 4-liter autoclave, purged with nitrogen flow at 70° C. for one hour, 75 ml of anhydrous hexane containing 800 mg of AlEt$_3$, 79.8 mg of dicyclopentyldimethoxysilane and 10 mg of solid catalyst component were introduced in propylene flow at 30° C. The autoclave was closed. 1.5 Nl of hydrogen were added and then, under stirring, 1.2 Kg of liquid propylene were fed. The temperature was raised to 70° C. in five minutes and the polymerization was carried out at this temperature for two hours. The non-reacted propylene was removed, the polymer was recovered and dried at 70° C. under vacuum for three hours and, then, weighed and fractionated with o-xylene to determine the amount of the xylene insoluble (X.I.) fraction at 25° C.

Determination of X.I.

2.5 g of polymer were dissolved in 250 ml of o-xylene under stirring at 135° C. for 30 minutes, then the solution was cooled to 25° C. and after 30 minutes the insoluble polymer was filtered. The resulting solution was evaporated in nitrogen flow and the residue was dried and weighed to determine the percentage of soluble polymer and then, by difference the Xylene-Insoluble (X.I.) fraction (%).

EXAMPLES

Examples 1–5 and Comparative Examples 6–9

Preparation of Solid Catalyst Components.

Into a 500 ml four-necked round flask, purged with nitrogen, 250 ml of $TiCl_4$ were introduced at 0° C. While stirring, 10.0 g of microspheroidal $MgCl_2*2.8C_2H_5OH$ (prepared according to the method described in ex.2 of U.S. Pat. No. 4,399,054 but operating at 3,000 rpm instead of 10,000) and 7.5 mmoles of malonate were added. The temperature was raised to 100° C. and maintained for 120 min. Then, the stirring was discontinued, the solid product was allowed to settle and the supernatant liquid was siphoned off.

250 ml of fresh $TiCl_4$ were added. The mixture was reacted at 120° C. for 60 min and, then, the supernatant liquid was siphoned off. The solid was washed six times with anhydrous hexane (6×100 ml) at 60° C. Finally, the solid was dried under vacuum and analyzed. The type and amount of malonate (wt %) and the amount of Ti (wt %) contained in the solid catalyst component are reported in Table 1. Polymerization results are reported in Table 2.

TABLE 1

| Ex. n. | Malonate Type | Wt % | Ti Wt % |
|---|---|---|---|
| 1 | Diethyl 2-(1-trifluoromethylethyl)-2-methylmalonate | 19.3 | 3.4 |
| 2 | Diethyl 2-(1-trifluoromethylethyl)malonate | 12.3 | 3.8 |
| 3 | Diethyl-2(1-trifluoromethylethyl)-2-benzylmalonate | 16.8 | 3.9 |
| 4 | Diethyl 2-(1-trifluoromethylethylidene)malonate | 11.4 | 3.7 |
| 5 | Bis(2-chloroethyl) 2-isopropylmalonate | 13.1 | 3.3 |
| Comp. 6 | Diethyl 2-isopropyl-2-methylmalonate | 12.2 | 3.1 |
| Comp. 7 | Diethyl 2-isopropylmalonate | 10.8 | 3.2 |
| Comp. 8 | Diethyl 2-isopropylidenemalonate | 9.6 | 3.1 |
| Comp. 9 | Diethyl 2-isopropyl-2-benzylmalonate | 19.7 | 4.7 |

TABLE 2

| Example n. | Yield KgPP/gCat | X.I. Wt % |
|---|---|---|
| 1 | 50 | 97.6 |
| 2 | 49 | 97.3 |
| 3 | 45 | 96.2 |
| 4 | 40 | 94.4 |
| 5 | 38 | 97.1 |
| Comp. 6 | 42 | 97.0 |
| Comp. 7 | 30 | 96.9 |
| Comp. 8 | 25 | 93.4 |
| Comp. 9 | 38 | 94.9 |

What is claimed is:

1. A solid catalyst component for the polymerization of olefins $CH_2=CHR$, in which R is hydrogen or a hydrocarbyl radical with 1–12 carbon atoms, comprising Mg, Ti, halogen and at least an heteroatom containing malonate of formula (I):

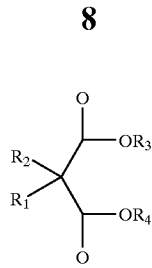

(I)

wherein $R_1$ and $R_2$, equal to or different from each other, are each H, a $C_{1-C20}$ linear or branched alkyl, alkenyl, cycloalkyl, aryl, arylalkyl or alkylaryl group and said $R_1$ and $R_2$ can also be joined to form a cyclic group; $R_3$ and $R_4$ are independently selected from $C_1-C_{20}$ linear or branched alkyl, alkenyl, cycloalkyl, aryl, arylalkyl or alkylaryl group and $R_3$ and $R_4$ can also be joined to form a cyclic group; with the proviso that at least one of the $R_1$ to $R_4$ groups contains at least one heteroatom selected from the group consisting of F, Cl, Br and Si, and that when $R_3$ and $R_4$ are $C_2$ alkyls, $R_1$ or $R_2$ do not contain O.

2. The solid catalyst component according to claim 1 in which $R_3$ and $R_4$ are primary alkyl, arylalkyl or alkylaryl groups having from 2 to 8 carbon atoms.

3. The solid catalyst component according to claim 2 which $R_3$ and $R_4$ are primary branched alkyl groups.

4. The solid catalyst component according to claim 1 in which at least one of $R_3$ and $R_4$ contain an heteroatom.

5. The solid catalyst component according to claim 1 in which $R_1$ is H and $R_2$ is a linear or branched $C_3-C_{20}$ alkyl, cycloalkyl, or arylalkyl group, optionally containing a heteroatom.

6. The solid catalyst component according to claim 5 in which $R_2$ is a $C_3-C_{20}$ secondary alkyl, cycloalkyl, or arylalkyl group.

7. The solid catalyst component according to claim 1 in which $R_1$ is H and $R_2$ is a $C_5-C_{20}$ primary linear or branched alkyl, a $C_5-C_{20}$ cycloalkyl, a $C_7-C_{20}$ arylalkyl or alkylaryl group.

8. The solid catalyst component according to claim 5 which $R_2$ contains a heteroatom.

9. The solid catalyst component according to claim 1 in which the heteroatom containing malonate is selected from the group consisting of diethyl 2-(1-trifluoromethylethyl) malonate, diethyl 2-(1-trifluoromethylethylidene)malonate, bis(2-chloroethyl) 2-isopropylmalonate, diethyl 2-(trimethylsilylmethyl)malonate, diethyl 2-p-chlorobenzylmalonate, diethyl 2-(1-trifluoromethyl-1-methylethyl)malonate, diethyl 2-α-phenyl-p-(trifluoromethyl)benzyl malonate, bis(2-fluoroethyl) 2-isopropylmalonate, bis(2-fluoroethyl) 2-ethylmalonate, diethyl-2-(1-trifluoromethylethyl)-2-benzylmalonate, diethyl 2-(1-trifluoromethylethyl)-2-methylmalonate, diethyl 2-(trimethylsilylmethyl)-2-methylmalonate, diethyl 2-p-chlorobenzyl-2-isopropylmalonate, diethyl 2-(1-trifluoromethyl-1-methylethyl)-2-methylmalonate, bis(2-trimethylsilylethyl) 2-isopropyl-2-isobutylmalonate, and bis (p-chlorobenzyl) 2-cyclohexyl-2-methylmalonate.

10. The solid catalyst component according to claim 1 in which both $R_1$ and $R_2$ are different from H and in which at least one of $R_1$ and $R_2$ is a primary $C_3-C_{20}$ alkyl, cycloalkyl, or arylalkyl group.

11. The solid catalyst component according to claim 1 comprising a titanium compound having at least a Ti-halogen bond and the heteroatom containing malonate supported on a Mg halide in active form.

12. The solid catalyst component according to claim 11 in which the titanium compound is $TiCl_4$ or $TiCl_3$.

13. The solid catalyst component according to claim 1 having a spherical form, a surface area (by B.E.T. method) between 20 and 500 m$^2$/g, and a total porosity (by B.E.T. method) higher than 0.2 cm$^3$/g.

14. The solid catalyst component according to claim 13, wherein the surface area (by B.E.T. method) is between 50 and 400 m$^2$/g, and the total porosity (by B.E.T. method) is between 0.2 and 0.6 cm$^3$/g.

* * * * *